United States Patent [19]

Judell

[11] 4,296,755
[45] Oct. 27, 1981

[54] METHOD AND APPARATUS FOR DETERMINING VENTRICULAR FIBRILLATION

[75] Inventor: Neil H. K. Judell, N. Kingstown, R.I.

[73] Assignee: Datamedix Inc., Boca Raton, Fla.

[21] Appl. No.: 131,587

[22] Filed: Mar. 19, 1980

[51] Int. Cl.³ .............................................. A61B 5/04
[52] U.S. Cl. ................................ 128/705; 128/419 D
[58] Field of Search ............................... 128/702–705, 128/419 D; 364/417

[56] References Cited

U.S. PATENT DOCUMENTS

| | | | |
|---|---|---|---|
| 3,598,110 | 8/1971 | Edmark | 128/703 |
| 3,612,041 | 10/1971 | Ragsdale | 128/705 |
| 3,654,916 | 4/1972 | Neilson | 128/704 |
| 3,848,586 | 11/1974 | Suzuki et al. | 364/417 |
| 4,022,192 | 5/1977 | Lavkien | 364/417 |

OTHER PUBLICATIONS

Nygards et al., "Computers in Cardiology", IEEE Computer Society, 1977, pp. 393–397.
Kuo et al., "Computers in Cardiology", IEEE Computer Society, 1978, pp. 347–349.
Makhoul, "Proceedings of the IEEE", vol. 63, No. 4, Apr. 1975, pp. 561–580.
Kyle et al., "Proceedings of the Conference on Applications of Electronics in Medicine", Southampton Hants Eng. 6-8, Apr. 1976, pp. 223–228.

*Primary Examiner*—William E. Kamm
*Attorney, Agent, or Firm*—Malin & Haley

[57] ABSTRACT

A method for declaring the presence of ventricular fibrillation from an incoming electrocardiograph signal includes sampling the signal at a first frequency and filtering the same to produce a secondary frequency lower than the first frequency. This filtered signal is passed to a linear predictor which fits a model signal spectrum to the actual signal spectrum and computes coefficients representative of bandwith and mean frequency of the signal over a short time interval. The method then includes comparing the coefficient of bandwith with a preselected threshold value to determine whether it exceeds same, and, if so, comparing the coefficient of mean frequency with a range of values to determine whether it falls within that range whereby ventricular fibrillation is then declared to be present.

An apparatus to carry out the method substantially as described above, is included in this invention.

30 Claims, 8 Drawing Figures

METHOD AND APPARATUS FOR DETERMINING VENTRICULAR FIBRILLATION

BACKGROUND OF THE INVENTION

The present invention generally relates to cardiac arrhythmia detectors, and more particularly, concerns a method and apparatus for determining and declaring the presence of ventricular fibrillation in an electrocardiograph signal which is being monitored.

In patients having cardiac problems or surgery, one of the major concerns is the potential for the onset of ventricular fibrillation. For whatever the reasons may be for causing ventricular fibrillation, its occurrence is a most serious event. The quivering of the ventricles associated with ventricular fibrillation causes cessation of the cardiac output. In a high percentage of patients ventricular fibrillation represents the terminal cardiac event. Although ventricular fibrillation is quite serious, it can be controlled or arrested by heart massage and defibrillation techniques. One well known defibrillation technique is the application of a severe electrical shock to the patient's heart which subdues the excitation of the ventricles. However, the defibrillation application must be performed quickly in order to overcome the cessation of cardiac output. This time period for the application of defibrillation must be within a few minutes from the onset of ventricular fibrillation. Therefore, monitoring the patient for purposes of detecting ventricular fibrillation is an important procedure involving cardiac patients.

Conventional bedside electrocardiograph (ECG) monitors in general are not adequate for reliable ventricular fibrillation detection. For instance, many heart rate meters are optimized to detect well defined QRS complexes, and may detect ventricular fibrillation waveforms as beats only sporadically, causing either a long delay before providing an alarm, or even worse, no alarm indication at all. Furthermore, ventricular fibrillation rates may be as low as one hundred twenty (120) beats per minute and may be below the upper heart rate alarm limit. Meters that reject T-waves pose problems because one half of the ventricular fibrillation waveform may be classified as a T-wave. Even some computerized arrhythmia monitoring systems have difficulty in providing reliable ventricular fibrillation detection if they employ noise detectors that do not distinguish a ventricular fibrillation period from a high noise period.

A number of apparatuses for detecting ventricular fibrillation by monitoring ECG waveforms have been proposed. Various types of these apparatuses have been described, for example, in U.S. Pat. Nos. 3,612,041 and 3,598,110. In the former patent, fibrillation is indicated when the signal occurs at a two hundred (200) to five hundred (500) beat per minute rate. As indicated above, ventricular fibrillation rates may be as low as one hundred twenty (120) beats per minute. In this instance, such ventricular fibrillation will be below the indication level relied upon by U.S. Pat. No. 3,612,041. In the latter patent mentioned above, the circuit seeks to establish permature ventricular contraction rather than ventricular fibrillation. Also, the circuitry is somewhat complex in nature. Another apparatus for monitoring recurrent waveforms to establish, for example, ventricular fibrillation, is disclosed in U.S. Pat. No. 3,654,916. However, in that patent, the abnormality of waveform complexes is relied upon to establish ventricular fibrillation as being present in the waveform. Various complicated steps to produce a voltage level related to the mean irregularity of shape of the ECG complex are required to establish that ventricular fibrillation is present.

Another more recent technique for detecting ventricular fibrillation has been proposed and involves the use of fast Fourier transforms (FFT's). An explanation of this technique is found in two recently published periodicals, Nygards, M. E., and Hulting, J., "Recognition of Ventricular Fibrillation Utilizing the Power Spectrum of the ECG," *Computers in Cardiology*, pages 393 to 397, IEEE Computer Society, 1977, and Kuo, S. and Dillman, R., "Computer Detection of Ventricular Fibrillation," *Computers in Cardiology*, pages 347 to 349, IEEE Computer Society, 1978. The basic notion associated with the FFT technique is to equate ventricular fibrillation with the presence of a sinusoidal signal; this is accomplished by examining the spectrum of the incoming ECG signal, determining its mean frequency and bandwith, and if these two measurements satisfy certain constraints, then ventricular fibrillation is declared to exist. While this technique appears to be quite accurate, it also has a number of deficiencies or limitations. For instance, the equipment and approach used in the FFT technique trade computational complexity for enhanced accuracy. The minimum computational cost for the known FFT technique has been estimated at $2N\log_2 N$ multiplies, the requirement for buffering N data words (the number of data points to be analyzed), and the complexity of programming FFT equipment. This computational cost in this large number of real multiplies does not include the determination of bandwith and mean frequency of the signal. As a result, these proposed FFT techniques employ large, complex computations that are generally impractical to be included in bedside cardiac monitors. Accordingly, it can be seen that the shortcomings in equipment and techniques to detect and declare the presence of ventricular fibrillation require improvements in this most significant component in the monitoring of cardiac patients.

SUMMARY OF THE INVENTION

A method for declaring the presence of ventricular fibrillation from an incoming electrocardiograph signal comprises sampling the signal at a first frequency. The signal is filtered to produce a more purified output signal at a second frequency lower than the first frequency. This method includes accumulating data, utilizing a technique of linear prediction, based on the filtered signal over a short time interval and computing coefficients representative of bandwith and mean frequency of the signal from the accumulated data with preferably a maximum of $3N+6$ real multiplies of computations where N represents the number of data points to be analyzed. A determination is made whether the filtered signal is substantially sinusoidal in character, and, if so, a determination is then made whether the computed coefficient of mean frequency lies within a preselected range of values whereby ventricular fibrillation is declared to be present.

In the preferred embodiment of this aspect of the present invention, the electrocardiograph signal is sampled at approximately 200 Hz. This sampled signal is passed through a low-pass filter to produce a decimated signal at approximately 25 Hz, which is then passed through a high-pass filter to substantially remove any direct current (DC) components and baseline wander.

The method preferably includes examining the spectrum of the filtered and modified signal by passing the same to a linear predictor which fits a model signal spectrum to the actual signal spectrum and then computes the aforementioned coefficients. By employing linear prediction, "spectral flatness" of the signal is examined and the linear predictor finds the model spectrum that minimizes the following relationship:

$$\frac{1}{2\pi} \int_0^{2\pi} \frac{S(w)dw}{S_0(w)}$$

where $S(w)$ is the actual signal spectrum and $S_0(w)$ is the model spectrum. The model spectrum has been preselected and utilizes the following preferred form:

$$S_0(w) = (1 + A1e^{-jw} + A2e^{-2jw})^{-1}(1 + A1e^{jw} + A2e^{2jw})^{-1}$$

coefficients, $A1$ and $A2$, are the parameters of the model spectrum, with $A1$ being representative of mean frequency of the monitored signal, and $A2$ being representative of signal bandwidth. If $x(1), x(2) \ldots x(N)$ is the input signal (generally representing data accumulated each second), then $A1$ and $A2$ are given by the following relationships:

$$A1 = \frac{RS - QR}{Q^2 - R^2}$$

$$A2 = \frac{R^2 - QS}{Q^2 - R^2}$$

where:

$$Q = \sum_{i=1}^{N} x^2(i)$$

$$R = \sum_{i=1}^{N-1} x(i)x(i+1)$$

$$S = \sum_{i=1}^{N-2} x(i)x(i+2)$$

$A2$, representative of bandwidth, is then compared with a preselected threshold value, preferably in a logic cirucit, and if exceeded that serves to indicate that the signal is substantially sinusoidal in character. Only when the input signal is substantially sinusoidal is ventricular fibrillation declared to be present. This sinusoidal character of the signal, however, is not the only criteria which establishes the presence of ventricular fibrillation. Mean frequency, $A1$, which has been calculated is compared to a preselected range of values, also preferably in a logic circuit. If this value of $A1$ falls within this preselected range, this serves as an indication that the substantially sinusoidal signal is in a frequency range between about 2 Hz and 12 Hz. When these two conditions of the coefficients of bandwidth and mean frequency are met, ventricular fibrillation is declared to be present. This declaration can be accomplished by providing an alarm or other indication that the signal has ventricular fibrillation present.

Another aspect of the present invention includes an apparatus for declaring the presence of ventricular fibrillation from an incoming electrocardiograph signal. This apparatus includes means for modifying the electrocardiograph signal to a more purified, low frequency sampling rate. Linear predictor means is adapted to receive the modified signal and accumulate data based on the signal over a short interval and compute coefficients representative of bandwith and mean frequency of the signal from the accumulated data with preferably a maximum of $3N+6$ real multiples of computations where N represents the number of data points to be analyzed. Utilizing the coefficients provided by the linear predictor means, the apparatus includes means for determining whether the modified signal is substantially sinusoidal in character and means for determining whether the computed coefficient of mean frequency falls within a preselected range of values. Also, there is means for declaring ventricular fibrillation to be present in the signal if a substantially sinusoidal signal has a mean frequency within the preselected range.

In the preferred embodiment of this aspect of the invention, the linear predictor includes elements associated with the current output of a high-pass digital filter to store certain multiplied values of the output current for one second of operation and to accumulate data over a short time interval, and to compute the aforementioned coefficients. These coefficients, $A1$ and $A2$, are substantially as described above and are preferably computed in the linear predictor in accordance with the mathematical relationships as set forth above. Comparators in a logic circuit take the computed values of $A1$ and $A2$ to determine whether or not the preselected comparison values have been attained. If so, the output is logic 1 (i.e., ventricular fibrillation is present) and if not, the output is logic 0 (ventricular fibrillation not present).

In accordance with the principles of the present invention, the method and apparatus herein overcome the deficiencies noted above with respect to prior art methods and techniques for detecting ventricular fibrillation in an electrocardiograph signal. The technique herein described in conjunction with this invention for detecting ventricular fibrillation is essentially equivalent to the FFT technique as far as accuracy and the low false alarm rates. However, in contrast to the FFT technique, the present invention is concerned solely with bandwidth and mean frequency of the signal, and does not require detailed information about the power spectrum of the signal. Accordingly, the present invention relies upon simple spectral estimation which requires, at most, $3N+6$ multiplies in the computations, including determination of bandwith and mean frequency, six buffer words and is simple to program. Using "spectral matching" properties of linear prediction, and a suitable model for the spectrum, the method and apparatus of the present invention can be used to reliably detect and declare ventricular fibrillation with a computational complexity easily handled by an inexpensive microprocessor. With this capability, the spectral estimator (linear predictor) can be used to detect ventricular fibrillation accurately within three seconds of onset, and is substantially immune to false detections with a variety of signals and in the presence of extreme artifact. A significant advantage of the present invention lies in its computational simplicity, which allows it to be constructed from very little hardware, or allows it to be emulated in a microprocessor based system in real time.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims.

Figure 1:
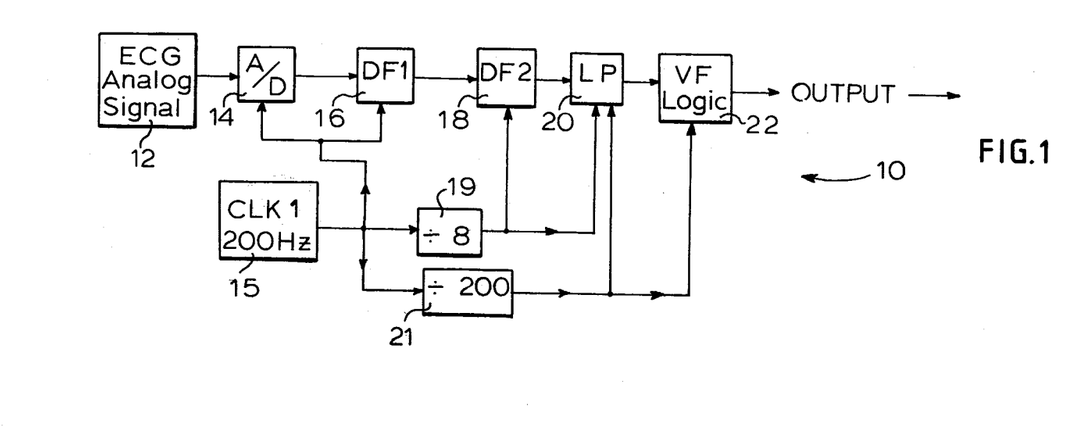
FIG. 1 is a block diagram schematically illustrating the functioning of the preferred apparatus for declaring the presence of ventricular fibrillation from an incoming electrocardiograph signal.

Adverting to the drawings, particularly FIG. 1, there is illustrated an overall block diagram of the preferred ventricular fibrillation detector 10 of the present invention. This schematical representation of the ventricular fibrillation detector shows the main components included therein. An electrocardiograph (ECG) analog signal 12 is provided from a standard ECG monitor which is connected to a patient and produces a signal associated with the heart action of the patient. The actual ECG equipment is not shown in the drawings herein inasmuch as it is not part of the present invention. This ECG analog signal is fed to ventricular fibrillation detector 10 and is converted to a digital signal by virtue of the analog to digital converter 14. A frequency clock 15 is provided to sample the digital signal at a preferred frequency of 200 Hz. A low-pass, digital filter 16 receives the sampled signal to permit a lower sampling rate of 25 Hz to be employed. At this lower sampling rate, the signal is passed to a high-pass, digital filter 18 that removes effects of baseline wander and DC offset. A second timing clock 19 is connected to high-pass filter 18 in order to produce a data rate of 25 Hz. After this modified, preconditioned signal passes through the filters, it is operated on by a linear predictor 20 which by spectral estimation analyzes data points from the signal to determine whether that signal can be characterized as including ventricular fibrillation. A third clock 21, in addition to second clock 19, is connected to the linear predictor so that the sampled frequency of 200 Hz can be divided by 200 in order to accumulate data for a period of approximately one second. Information and data analyzed by linear predictor 20 is provided to ventricular fibrillation logic circuit 22 in order to actually make a declaration if ventricular fibrillation is present in the signal. Once again, the "divide by" 200 clock 21 is associated with logic circuit 22 in order to be compatible with the one second data analysis of the linear predictor. The declaration made by logic circuit 22 is the output which would be transmitted to an alarm or other indication device to inform the user that ventricular fibrillation is present.

Figure 2:
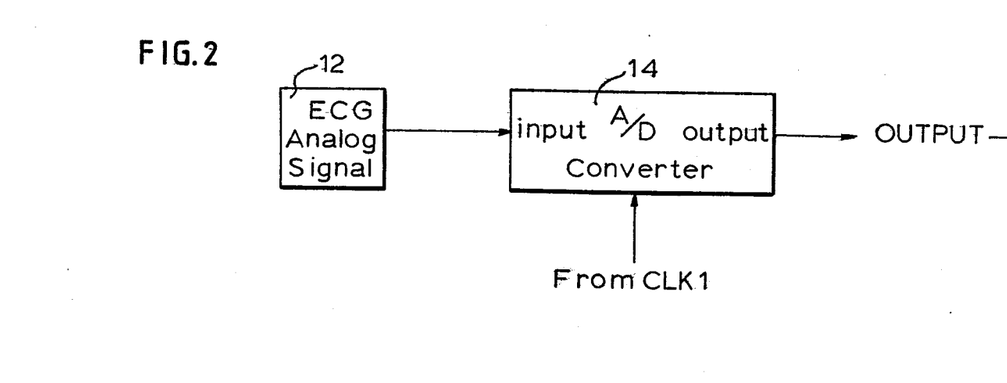
FIG. 2 is a block diagram schematically illustrating the analog to digital converter of FIG. 1.

In FIG. 2, analog to digital converter 14 is illustrated as receiving an ECG analog signal 12 from an ECG source while being clocked at 200 Hz. This type of analog to digital converter is well known in the art and may be selected according to the requirements of this invention. Output from the analog to digital converter 14 is then connected to the low-pass digital filter.

Figure 3:
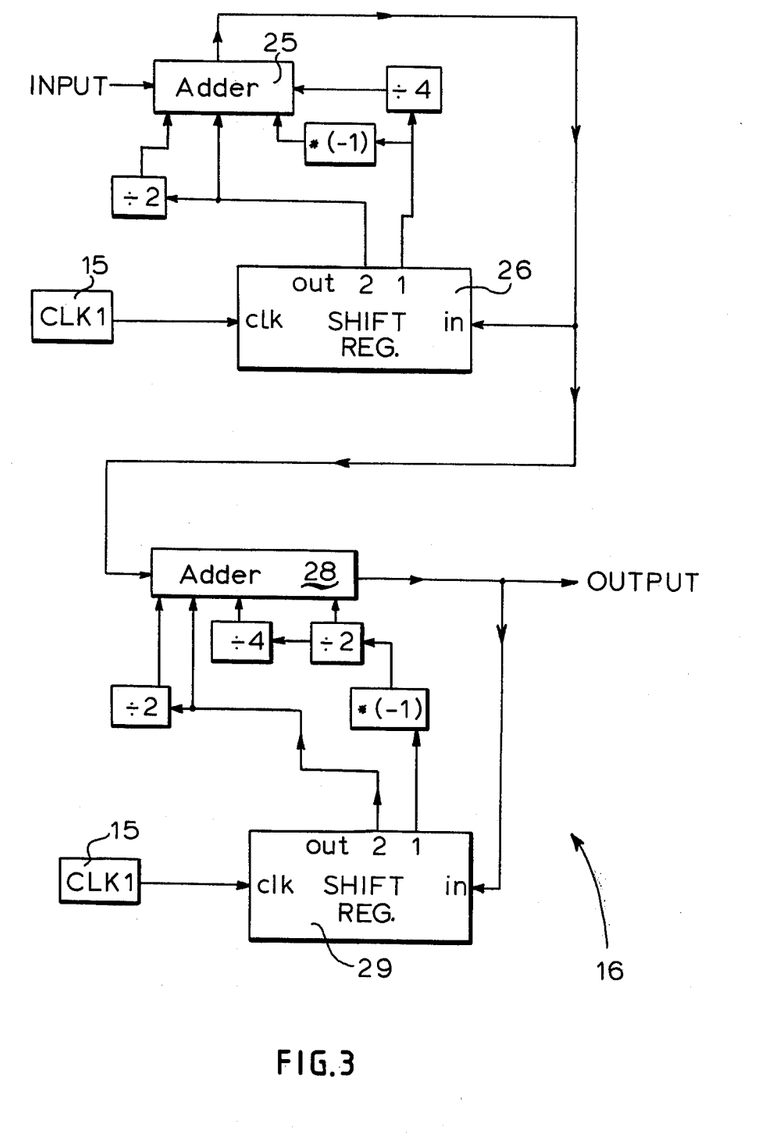
FIG. 3 is a block diagram schematically illustrating the functioning of the low-pass, digital filter DF1 of FIG. 1.

Referring to FIG. 3, the details of low-pass digital filter 16 are illustrated. Basically, the low-pass, digital filter 16 is a two section recursive digital filter. Each section's output is the sum of the current input value and the previous two output values associated with the sampling rate of 200 Hz. Input from the analog to digital converter is provided to an adder element 25, the output of which is transmitted to a shift register 26 and to a similar adder element 28 in the other section of the recursive filter. Frequency clock 15 controls the sampling rate of shift register 26. Adder 28 in the second part of the recursive filter receives as its input the data from adder 25, while also receiving the accumulated data from shift register 29 similar to shift register 26. As a result, this low-pass filter combination produces an output at a 200 Hz rate, with a bandwith of approximately 12 Hz. In addition, this low-pass filter prevents AC line interference from causing false ventricular fibrillation alarms and also allows sufficient down sampling so as not to overload the microprocessor. Furthermore, after filtering at the 200 Hz rate, only every eighth data point will be outputted to high-pass filter 18. The "divide by" elements illustrated in FIG. 3 provide the means for decimating the 200 Hz signal to a rate of 25 Hz. This output is then passed to high-pass filter 18.

Figure 4:
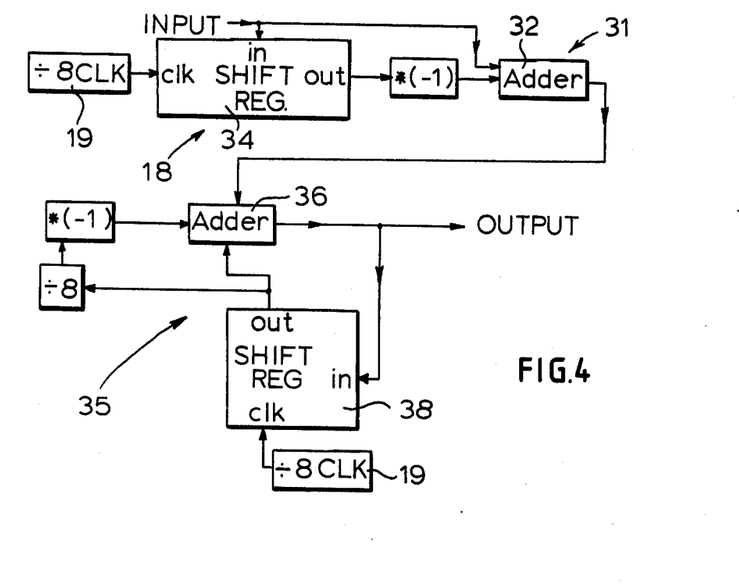
FIG. 4 is a block diagram schematically illustrating the functioning of a high-pass digital filter DF2 of FIG. 1.

Turning now to FIG. 4, the particular details of high-pass filter 18 are illustrated. This high-pass filter is preferably a 0.6 Hz, sharp cut-off high-pass filter which contributes to the removal of effects of baseline wander of the signal and DC offset. High-pass filter 18 generally includes two sections, the first filter section 31 receiving, as its input, the signal from the low-pass digital filter into adder element 32. The "divide by" 8 clock 19 is also connected to adder element 32 through a shift register 34 in order to provide a data rate of 25 Hz. The output of first filter section 28 produces a signal equal to the difference between the previous input value and the current input value, thus the inclusion of shift register 34. Output from adder 32 is provided to the second filter section 35 and specifically into an adder element 36. The "divide by" 8 clock 19 clocks the signal at a data rate of 25 Hz and the shift register 38 is provided so that this second filter section 35 can operate as a linear combination of the output of this second filter section. After passing through second filter section 35, the output of this highpass digital filter is at a 25 Hz rate, and it is this preconditioned signal which is transmitted to the linear predictor, more clearly illustrated in FIGS. 5 and 6.

Figure 5:
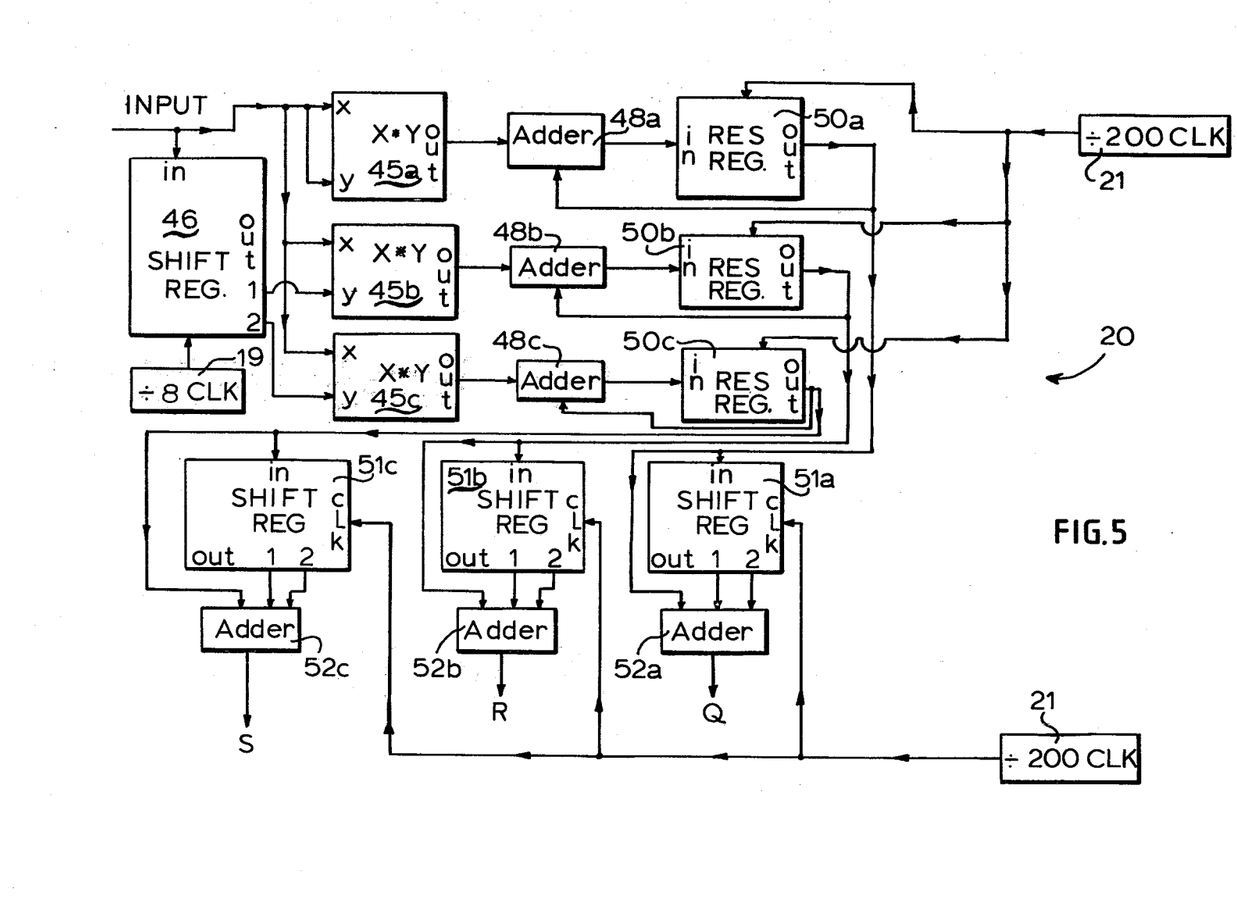
FIG. 5 is a block diagram schematically illustrating part of the functioning of the linear predictor LP of FIG. 1.
Figure 6:
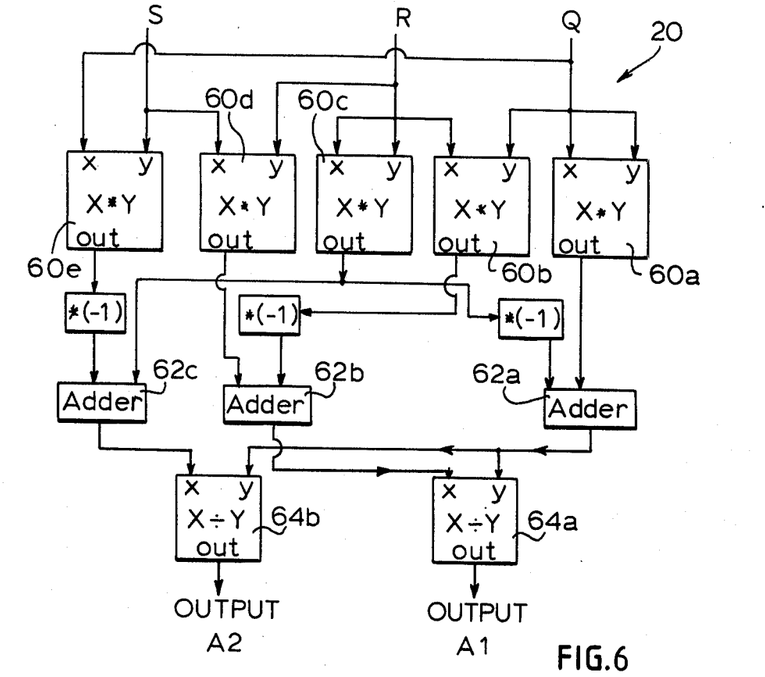
FIG. 6 is a block diagram schematically illustrating the remaining function of the linear predictor LP of FIG. 1.

In FIGS. 5 and 6, the working elements of the linear predictor 20 are more clearly illustrated. Linear predictor 20 serves as a mechanism for employing spectral estimation with respect to the incoming signal for purposes of determining whether that signal may include a characteristic representative of ventricular fibrillation. In this linear predictor, a model signal spectrum is fitted to the actual signal spectrum by what is known as "spectral flatness." To this end, linear predictor 20 finds the model signal spectrum that minimizes the following relationship:

$$\frac{1}{2\pi} \int_0^{2\pi} \frac{S(w)dw}{S_0(w)}$$

where S(w) is the actual signal spectrum and $S_0(w)$ is the model spectrum. Inasmuch as the model spectrum can be selected for purposes of the function at hand, the following model signal spectrum has been preferably selected, so that:

$$S_0(w) = (1 + A1e^{-jw} + A2e^{-2jw})^{-1}(1 + A1e^{jw} + A2e^{2jw})^{-1}$$

In this model, A1 and A2 are the parameters of the model, with the coefficient A1 being representative of the mean frequency of the signal, and the coefficient A2 being an indicator of the bandwith of the signal. However, in order to compute the coefficients A1 and A2, a number of data points from the incoming signal must be analyzed and accumulated over a short time invterval to associate these data points with ventricular fibrillation if the coefficients computed from these data points meet certain requirements.

Particularly referring to FIG. 5, the first portion of linear predictor 20 illustrates the computation of intermediate values of Q, R and S from the data points analyzed in the process of computing coefficients A1 and A2. Intermediate values Q, R and S are defined mathematical relationships which are computed from the current output from the high-pass digital filter over a short time interval. Q, R and S may be defined as follows:

$$Q = \sum_{i=1}^{N} x^2(i)$$

$$R = \sum_{i=1}^{N-1} x(i)x(i+1)$$

$$S = \sum_{i=1}^{N-2} x(i)x(i+2)$$

where x(i) is the current output of the input signal being analyzed approximately once per second over the time period x(1), x(2) ... x(N). FIG. 5 illustrates the elements of the linear predictor which operate on the current output of the high-pass filter to store the various multiplied values of the output current for each one second of operation. The signal is inputted from the high-pass digital filter to three multipliers 45a, b and c. The output from shift register 46 is provided to multipliers 45b and c to provide data input at a different time frame. Note that shift register 46 is clocked by the "divide by" 8 clock 19 so that the sampling rate is at 25 Hz. In this arrangement, the outputs of the three multipliers are the square of the current output of the high-pass filter; the product of the current value and the previous value; and the product of the current value and the second previous value. These values from the multipliers are added in adder elements 48a, b and c and then accumulated in the three registers 50a, b and c over one period of the "divide by" 200 clock 21, i.e., for one second. From these registers wherein the data values are accumulated, the data is passed to shift registers 51a, b and c and adders 52a, b and c which form three second accumulations of each of the accumulated values from registers 50a, b and c. As a result of the arrangement of these computational elements, the intermediate values of Q, R and S are produced.

Based on the model signal spectrum selected, coefficients A1 and A2 are derived from a simple form of linear prediction satisfying the following relationship:

$$\begin{bmatrix} Q & R & S \\ R & Q & R \\ S & R & Q \end{bmatrix} \begin{bmatrix} 1 \\ A1 \\ A2 \end{bmatrix} = \begin{bmatrix} X \\ 0 \\ 0 \end{bmatrix}$$

Solving this determinant, A1 and A2 are computed as follows:

$$A1 = \frac{RS - QR}{Q^2 - R^2}$$

$$A2 = \frac{R^2 - QS}{Q^2 - R^2}$$

FIG. 6 illustrates the multipliers 60a, b, c, d and e, adders 62a, b and c, and divider elements 64a and b in a proper arrangement for the computation of coefficients A1 and A2 according to the previously set forth relationship. The output from linear predictor 20 then becomes the computed values of A1 and A2 which is then passed to logic circuit 22. In calculating the values of A1 and A2, representative of mean frequency and bandwidth of the signal, respectively, the linear predictor requires only 3N+6 real multiplies, where N equals the number of data points to be analyzed. Determination of bandwith and mean frequency are included in this number of real multiplies of computations. In addition, in programming these computations in a microprocessor, rotating buffers of the intermediate values of Q, R and S may be employed, so that only nine accumulating buffers would be required. This leads to a simplification of the computer program to carry out the computational steps herein.

Figure 7:
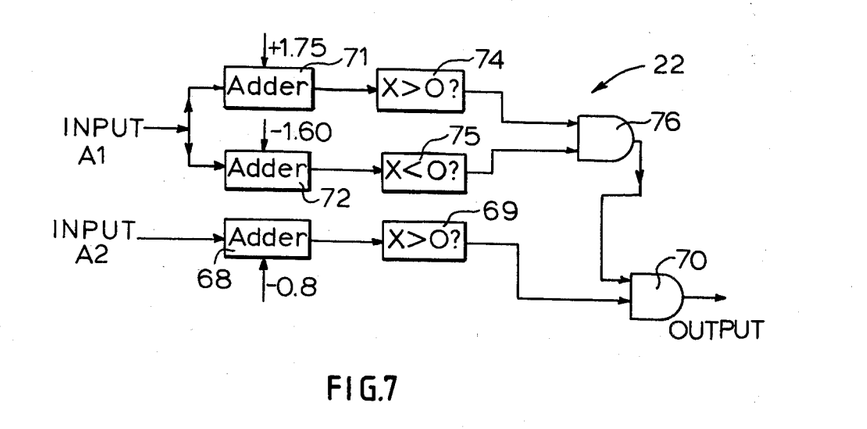
FIG. 7 is a block diagram schematically illustrating the logic circuit for the declaration of the presence of ventricular fibrillation in the incoming signal.
Figure 8:
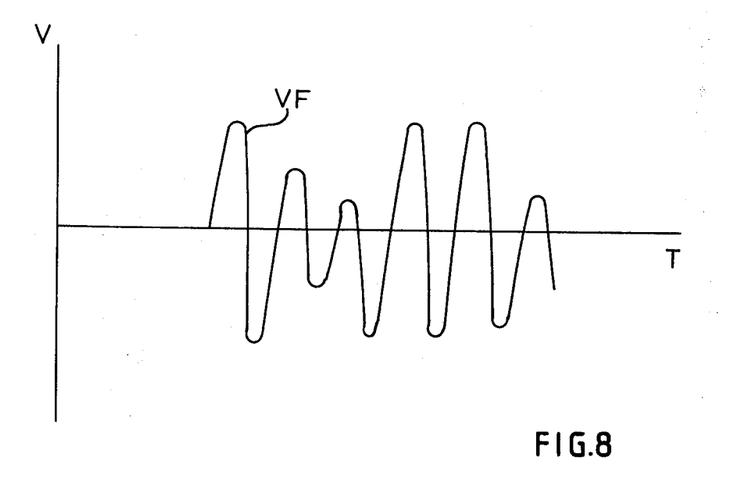
FIG. 8 is a graphic representation of a typical electrocardiogram during ventricular fibrillation.

The purpose of the analysis of the data points and the computations described above is to determine whether the incoming signal from the electrocardiograph is substantially sinusoidal in character. One of the prerequisites for a determination of the presence of ventricular fibrillation is that the incoming ECG signal from the patient being monitored take on a substantially sinusoidal form. FIG. 8 shows an incoming ECG waveform which is typical when ventricular fibrillation (VF) is present. In order to determine whether a sinusoidal waveform is present in the signal, "spectral flatness" is employed. To make this determination, the roots of the Z-transform polynomial, $Z^2 + A1Z + A2$, are analyzed. If the quantity $A1^2 - 4A2$ is greater than zero, then the roots of the Z-transform polynomial are real, and the signal is not at all sinusoidal and therefore ventricular fibrillation is not present. However, if the roots of this polynomial are complex, then A2 is greater than 0, with A2 being an indicator of bandwith. If A2 is approximately 0, the spectrum is nearly flat, while if A2 is nearly equal to 1, the spectrum of the signal is substantially sinusoidal. Accordingly, a substantially sinusoidal signal can be declared if the value of coefficient A2 is nearly equal to 1. It has been determined that a threshold value of 0.8 would provide a reliable indication that the ECG signal has a form substantially sinusoidal in character. Accordingly, as illustrated in FIG. 7, the A2 value from linear predictor 20 is fed into logic circuit 22 to adder element 68 which adds the value minus 0.8 to the computed value of coefficient A2. Following this addition step, the value is provided to a comparator 69 which determines whether the added sum is greater than 0, which when taking the adder into account, essentially means that the coefficient A2 is greater than the preselected threshold value of 0.8. If this threshold value is exceeded, the signal passes to logic output 70. If the threshold value is not reached, no signal is passed to logic output 70, inasmuch as ventricular fibrillation is declared not to be present. In this instance, the equipment may be designed to provide an indication that ventricular fibrillation is not present in some type of affirmative indication, such as a certain color light or other signal.

In addition to the bandwith of the incoming ECG signal as an indication of ventricular fibrillation, it has been determined that ventricular fibrillation is present when the mean frequency of the incoming signal lies within a certain range. This frequency range lies between approximately 2 and 12 Hz. As described above, coefficient A1 is representative of the mean frequency of the signal and its computed value from linear predictor 20 is provided to logic circuit 22. In accordance with the model selected, the mean frequency of the signal is related to the parameters of the model according to the following relationship:

$$\cos(2\pi f_m/f_s) = -A1/2 \sqrt{A2}$$

where $f_m$ is the mean frequency of the signal and $f_s$ is the sampling rate of the signal (preferably 25 Hz). If ventricular fibrillation is present in the signal when the signal is sinusoidal and the frequency is between 2 and 12 Hz, coefficient A2 is given as approximately equal to 1, and the coefficient A1 is calculated as having a value of $-1.75$ if the mean frequency is at 2 Hz and $+1.60$ if the mean frequency is at 12 Hz. Accordingly, logic circuit 22 is designed to evaluate the coefficient A1 to determine whether it falls within the range of $-1.75$ to $+1.60$. To accomplish this evaluation, adder elements 71 and 72 as seen in FIG. 7 add in the respective lower and higher values to the computed A1 coefficient and pass these values to comparators 74 and 75 to determine whether the added sums are greater or less than 0, respectively. If the computed value of A1 falls within this range, the signal is passed to logic output 76. If this condition is satisfied, the output signal from logic output 76 is logic 1, which is then fed to output logic 70. If the range of values for the mean frequency is not met, then the output signal from logic output 76 is logic 0, which would serve as an indication that ventricular fibrillation is not present. If the respective comparators provide a signal to logic output 70 that the computed values of A1 and A2 meet the preselected requirements programmed into the logic circuit, the output signal from logic output 70 is logic 1, therefore serving as an indication that ventricular fibrillation is present in the ECG signal. This output may be provided to an alarm circuit (not shown) whereby an audio or visual signal may be activated to inform an attendant for the patient that ventricular fibrillation is present. It can be seen that logic output 70 will not produce a positive output signal unless both conditions of coefficients A1 and A2 have been met.

Thus, the present invention provides a method and apparatus for declaring the presence of ventricular fibrillation from an incoming electrocardiograph signal. Computational simplicity is featured in this invention, along with minimized computational cost for making the determination of the presence of ventricular fibrillation. The elements of this invention may be embodied in a microprocessor which is convenient for utilization with conventional ECG bedside monitors.

What is claimed is:

1. A method for declaring the presence of ventricular fibrillation from an incoming electrocardiograph signal comprising:

sampling said signal at a first frequency;

filtering said sampled signal to produce an output signal at a second frequency lower than said first frequency and to remove any DC components and baseline wander;

examining the spectrum of said filtered signal by passing the same to a linear predictor which fits a model signal spectrum to the actual signal spectrum and computes coefficients representative of bandwith and mean frequency of said signal over a short time interval; and comparing said coefficient of bandwith with a preselected threshold value to determine whether it exceeds same, and comparing said coefficient of mean frequency with a range of values to determine whether it falls within said range, and if both said determinations are positive, declaring ventricular fibrillation to be present.

2. The method of claim 1 wherein said examining step includes providing the filtered signal to said linear predictor and computing said coefficients approximately once each second.

3. The method of claim 2 wherein said computing step includes accumulating data during each second of said short time interval and basing said coefficients on said accumulated data.

4. The method of claim 3 wherein said computing step includes calculating a coefficient representative of mean frequency, A1, and a coefficient representative of signal bandwith, A2, based on the following relationship:

$$A1 = \frac{RS - QR}{Q^2 - R^2}$$

$$A2 = \frac{R^2 - QS}{Q^2 - R^2}$$

where:

$$Q = \sum_{i=1}^{N} x^2(i)$$

$$R = \sum_{i=1}^{N-1} x(i)x(i+1)$$

$$S = \sum_{i=1}^{N-2} x(i)x(i+2)$$

where $x(i)$ is the input signal analyzed approximately once per second over the time period $x(1), x(2) \ldots x(N)$.

5. The method of claim 4 wherein A1 and A2 are parameters of said model signal spectrum and said examining step includes finding the model signal spectrum that minimizes the following relationship:

$$\frac{1}{2\pi} \int_0^{2\pi} \frac{S(w)dw}{S_O(w)}$$

where S(w) is the actual signal spectrum and $S_O(w)$ is the model signal spectrum according to the following preselected relationship:

$$S_O(w)=(1+A1e^{-jw}+A2e^{-2jw})^{-1}(1+A1e^{jw}+A2e^{2jw})^{-1}$$

6. The method of claim 4 wherein said comparing step includes determining whether the coefficient representative of bandwidth, A2, is greater in its calculated value than about 0.8 which serves as an indication that said signal is substantially sinusoidal in character.

7. The method of claim 6 wherein said comparing step includes comparing the computed value of A1 from said linear predictor to determine whether it lies within a range of values according to the following relationship: $A1=2\sqrt{2}\times\cos(2\pi f_m/f_s)$, where $f_m$ is the mean frequency of the signal with preselected lower and upper limits, and $f_s$ is the sampling rate of the signal, and if said computed value of A1 falls within said range and A2 is greater than about 0.8, declaring ventricular fibrillation to be present.

8. The method of claim 1 wherein the comparing step includes outputting the values of said coefficients to a logic circuit.

9. The method of claim 8 wherein the declaring step includes said logic circuit providing a positive indication when said coefficients meet the preselected requirements for ventricular fibrillation to be present in said signal.

10. The method of claim 9 wherein said indication includes an alarm which is activated to inform a user that ventricular fibrillation is present in said signal.

11. A method for declaring the presence of ventricular fibrillation from an incoming electrocardiograph signal comprising the following steps in the order listed:
sampling said signal at approximately 200 Hz;
passing said sampled signal through a low-pass filter to decimate its output signal to approximately 25 Hz;
passing said decimated signal through a high-pass filter to substantially remove any DC components and baseline wander, the output from the high-pass filter being at approximately 25 Hz;
examining the spectrum of said 25 Hz signal by passing same to a linear predictor which fits a model signal spectrum to the actual signal spectrum and computes coefficients representative of bandwidth and mean frequency of said signal over a short time period; and
comparing said coefficient of bandwidth with a preselected threshold value to determine whether it exceeds same, and comparing said coefficient of mean frequency with a range of values to determine whether it falls within said range, and if both said determinations are positive, declaring ventricular fibrillation to be present.

12. A method for declaring the presence of ventricular fibrillation from an incoming electrocardiograph signal comprising:
sampling said signal at a first frequency;
filtering said signal to produce a more purified output signal at a second frequency lower than said first frequency;
accumulating data based on said filtered signal over a short time interval and computing coefficients representative of bandwith and mean frequency of said signal from said accumulated data by means of linear prediction; and
determining whether said filtered signal is substantially sinusoidal in character by utilizing said computed coefficients, and, if so, determining whether said computed coefficient of mean frequency lies within a preselected range of values whereby ventricular fibrillation is declared to be present.

13. The method of claim 12 wherein said coefficients are computed with a maximum of $3N+6$ real multiplies of computations where N represents the number of data points to be analyzed.

14. A method for declaring the presence of ventricular fibrillation from an incoming electrocardiograph signal comprising:
sampling said signal at a first frequency;
filtering said signal to produce a more purified output signal at a second frequency lower than said first frequency;
comparing a model signal spectrum to the actual signal spectrum and finding the model signal spectrum that minimizes the following relationship:

$$\frac{1}{2\pi} \int_0^{2\pi} \frac{S(w)dw}{S_O(w)}$$

where S(w) is the actual signal spectrum and $S_O(w)$ is the model signal spectrum according to the following preselected relationship:

$$S_O(w)=(1+A1e^{-jw}+A2e^{-2jw})^{-1}(1+A1e^{jw}+A2e^{2jw})^{-1}$$

whereby said comparing step is performed by linear prediction;
computing the values of A1 as representative of mean frequency of said signal and A2 as representative of signal bandwith based on the following relationships:

$$A1 = \frac{RS - QR}{Q^2 - R^2}$$

$$A2 = \frac{R^2 - QS}{Q^2 - R^2}$$

where:

$$Q = \sum_{i=1}^{N} x^2(i)$$

$$R = \sum_{i=1}^{N-1} x(i)x(i+1)$$

$$S = \sum_{i=1}^{N-2} x(i)x(i+2)$$

where x(i) is the input signal analyzed approximately once per second over the time period x(1), x(2) ... x(N);
comparing the computed value of A2 to determine whether it is greater than a threshold value of about 0.8 which serves as an indication that said signal is substantially sinusoidal in character;

comparing the computed value of A1 to determine whether it lies within a range of values according to the following relationship: $A1 = -2\sqrt{2} \times \cos(2\rho f_m/f_s)$, where $f_m$ is mean frequency of the signal with preselected lower and upper limits, and $f_s$ is the sampling rate of the signal;

declaring ventricular fibrillation to be present if a substantially sinusoidal signal as determined has a mean frequency between said preselected lower and upper mean frequency limits.

15. The method of claims 4, 11 or 14 wherein the declaring of the presence of ventricular fibrillation is accomplished with a maximum of $3N+6$ real multiplies of computations in said linear predictor where N represents the number of data points to be analyzed.

16. The method of claims 7 or 14 wherein the preselected lower and upper limits of said mean frequency are 2 Hz and 12 Hz, respectively, and the sampling rate of said signal is 25 Hz.

17. An apparatus for declaring the presence of ventricular fibrillation from an incoming electrocardiograph signal comprising:
means for sampling said signal at a first frequency;
means for filtering said sampled signal to produce an output signal at a second frequency lower than said first frequency and to remove any DC components and baseline wander;
linear predictor means for fitting a model signal spectrum to the actual filtered signal spectrum and for computing coefficients representative of bandwith and mean frequency of said signal over a short time interval;
means for determining whether said coefficient of bandwith exceeds a preselected threshold value;
means for determining whether said coefficient of mean frequency falls within a preselected range of values; and
means for declaring ventricular fibrillation to be present in said signal when said preselected values of said coefficients are achieved.

18. The apparatus of claim 17 wherein said means for sampling includes an analog to digital converter adapted to sample said electrocardiograph signal at a first frequency.

19. The apparatus of claim 18 wherein said elements include multipliers, data registers, shift registers and adders to calculate a coefficient representative of mean frequency, A1, and a coefficient representative of signal bandwith, A2, based on the following relationships:

$$A1 = \frac{RS - QR}{Q^2 - R^2}$$

$$A2 = \frac{R^2 - QS}{Q^2 - R^2}$$

where:

$$Q = \sum_{i=1}^{N} x^2(i)$$

$$R = \sum_{i=1}^{N-1} x(i)x(i+1)$$

$$S = \sum_{i=1}^{N-2} x(i)x(i+2)$$

where $x(i)$ is the input signal from said second filter analyzed approximately once per second over the time period $x(1), x(2) \ldots x(N)$.

20. The apparatus of claim 19 wherein said means for determining whether said coefficient of bandwith exceeds a preselected threshold value includes a first logic comparator adapted to compare the computed value of said coefficient of bandwith with a value of about 0.8 and provide an indication if said threshold value is reached.

21. The apparatus of claim 20 wherein said means for determining whether said coefficient of mean frequency falls within a preselected range of values includes a second logic comparator adapted to compare the computed value of said coefficient of mean frequency from said linear predictor means with a range of values according to the following relationship: $A1 = -2\sqrt{2} \times \cos(2\pi f_m/f_s)$, where $f_m$ is the mean frequency of the signal with preselected lower and upper limits, and $f_s$ is the sampling rate of the signal, and provide an indication if said computed value of the mean frequency coefficient from the linear predictor means lies within said range of values in the second logic comparator.

22. The apparatus of claim 21 wherein said lower sampling frequency of the signal is approximately 25 Hz and the preselected lower and upper limits of said mean frequency are 2 Hz and 12 Hz, respectively.

23. The apparatus of claim 21 wherein said means for declaring includes a logic circuit associated with said comparators to provide a positive indication when said coefficients meet said preselected requirements for ventricular fibrillation to be present in said signal.

24. The apparatus of claim 23 wherein said indication includes an alarm which is activated to inform a user that ventricular fibrillation is present in said signal.

25. The apparatus of claim 19 wherein said linear predictor is adapted to provide information to the declaring means for the declaration of ventricular fibrillation after a maximum of $3N+6$ real multiplies where N represents the number of data points to be analyzed.

26. The apparatus of claim 16 wherein said filtering means includes a first filter being a low-pass digital filter adapted to decimate its output to a second sampling frequency lower than said first frequency, and further includes a second filter being a high-pass digital filter adapted to remove any DC components and baseline wander, the output from said second filter being directed to said linear predictor means.

27. The apparatus of claim 26 wherein said linear predictor means includes elements associated with the current output of said second filter to store certain multiplied values of said current output for one second of operation and to accumulate data over a short time interval, and to compute said coefficients of bandwith and mean frequency from said accumulated data.

28. The apparatus of claim 27 wherein said linear predictor means is adapted to compute coefficients of bandwith and mean frequency at the end of a three second time interval of accumulated data so that same can be outputted to said declaring means for declaration of the presence of ventricular fibrillation if the preselected values for the coefficients are achieved during computation.

29. An apparatus for declaring the presence of ventricular fibrillation from an incoming electrocardiograph signal comprising:

means for modifying said signal to a more purified, low frequency sampling rate;

linear predictor means adapted to receive said modified signal and accumulate data based on said signal over a short interval and compute coefficients representative of bandwith and mean frequency of said signal from said accumulated data;

means for determining whether said modified signal is substantially sinusoidal in character utilizing the coefficients computed by the linear predictor means;

means for determining whether said computed coefficient of mean frequency falls within a preselected range of values; and means for declaring ventricular fibrillation to be present in said signal if a substantially sinusoidal signal having a mean frequency within said preselected range of values is detected.

30. The apparatus of claim 29 wherein said linear predictor means includes means to compute said coefficients with a maximum of 3 N+6 real multiplies of computations where N represents the number of data points to be analyzed.

* * * * *